(12) United States Patent
Nishimura et al.

(10) Patent No.: US 11,103,219 B2
(45) Date of Patent: Aug. 31, 2021

(54) ULTRASOUND DIAGNOSTIC APPARATUS WITH ELECTROMAGNETIC NOISE SUPPRESSION

(71) Applicant: Konica Minolta, Inc., Tokyo (JP)

(72) Inventors: Yushi Nishimura, Hachioji (JP); Masashi Kunita, Yokohama (JP); Yoshihiko Ito, Yamato (JP); Mutsuhiro Akahane, Ome (JP); Yasuhiro Nakamura, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 986 days.

(21) Appl. No.: 14/989,359

(22) Filed: Jan. 6, 2016

(65) Prior Publication Data

US 2016/0199039 A1    Jul. 14, 2016

(30) Foreign Application Priority Data

Jan. 9, 2015    (JP) .............................. JP2015-002790

(51) Int. Cl.
*A61B 8/00* (2006.01)
*A61B 8/06* (2006.01)
(Continued)

(52) U.S. Cl.
CPC .................. *A61B 8/54* (2013.01); *A61B 8/06* (2013.01); *A61B 8/4488* (2013.01); *A61B 8/488* (2013.01);
(Continued)

(58) Field of Classification Search
CPC ......... A61B 8/54; A61B 8/488; A61B 8/4488; A61B 8/4494
See application file for complete search history.

(56) References Cited

U.S. PATENT DOCUMENTS

| | | | | |
|---|---|---|---|---|
| 4,285,011 A | * | 8/1981 | Sato | G01S 7/5205 348/163 |
| 4,893,284 A | * | 1/1990 | Magrane | G01S 7/5205 367/12 |

(Continued)

FOREIGN PATENT DOCUMENTS

| | | | |
|---|---|---|---|
| JP | S60-129036 | * | 7/1985 |
| JP | S60-129036 A | | 7/1985 |

(Continued)

OTHER PUBLICATIONS

Official Notification of Refusal dated Nov. 6, 2018 from the corresponding Japanese Patent Application No. 2015-002790 and English translation.

(Continued)

*Primary Examiner* — Serkan Akar
*Assistant Examiner* — Aminah Asghar
(74) *Attorney, Agent, or Firm* — Lucas & Mercanti, LLP

(57) ABSTRACT

An ultrasound diagnostic apparatus includes the following. A deflection controller generates delay time information to make phases of reception signals input to channels uniform according to a deflection angle. A channel selector selects a channel in which the reception signal is turned on or off so that the phases of the reception signals input to channels are different and which generates channel selection information. A reception delay interrupter provides the delay amount to the reception signal and which turns on or off the reception signal. An adder adds the plurality of reception signals which are provided with the delay amount and turned on.

8 Claims, 12 Drawing Sheets

(51) Int. Cl.
*G01S 15/89* (2006.01)
*G01S 7/52* (2006.01)
*A61B 8/08* (2006.01)
*G10K 11/34* (2006.01)

(52) U.S. Cl.
CPC .......... *A61B 8/5207* (2013.01); *A61B 8/5223* (2013.01); *A61B 8/5269* (2013.01); *G01S 7/52046* (2013.01); *G01S 7/52077* (2013.01); *G01S 15/8915* (2013.01); *G01S 15/8979* (2013.01); *G10K 11/346* (2013.01); *A61B 8/4472* (2013.01); *A61B 8/4494* (2013.01)

(56) References Cited

U.S. PATENT DOCUMENTS

| | | | | |
|---|---|---|---|---|
| 5,421,333 A * | 6/1995 | Takamizawa | ....... | G01S 7/52046 600/447 |
| 6,258,031 B1 * | 7/2001 | Sunagawa | .............. | A61B 8/488 600/443 |
| 2004/0210137 A1 * | 10/2004 | Baba | ................... | G01S 7/52034 600/443 |
| 2006/0241464 A1 * | 10/2006 | Ohtake | .................... | A61B 8/06 600/457 |
| 2008/0021324 A1 * | 1/2008 | Seto | ........................ | A61B 8/00 600/447 |
| 2011/0295119 A1 * | 12/2011 | Miller | ................. | G01S 15/8925 600/443 |
| 2012/0130246 A1 * | 5/2012 | Haider | ................. | A61B 8/4477 600/447 |
| 2013/0109968 A1 * | 5/2013 | Azuma | ................ | A61B 8/5269 600/441 |
| 2015/0351720 A1 * | 12/2015 | Ikeda | ................... | A61B 8/5207 600/447 |

FOREIGN PATENT DOCUMENTS

| | | | |
|---|---|---|---|
| JP | H10-075954 | * | 3/1998 |
| JP | H10-075954 A | | 3/1998 |
| JP | 2006223612 A | | 8/2006 |
| JP | 5459976 B2 | | 1/2014 |

OTHER PUBLICATIONS

Japanese Office Action dated Apr. 23, 2019 from corresponding Japanese Patent Application No. 2015-002790 and English translation.

* cited by examiner

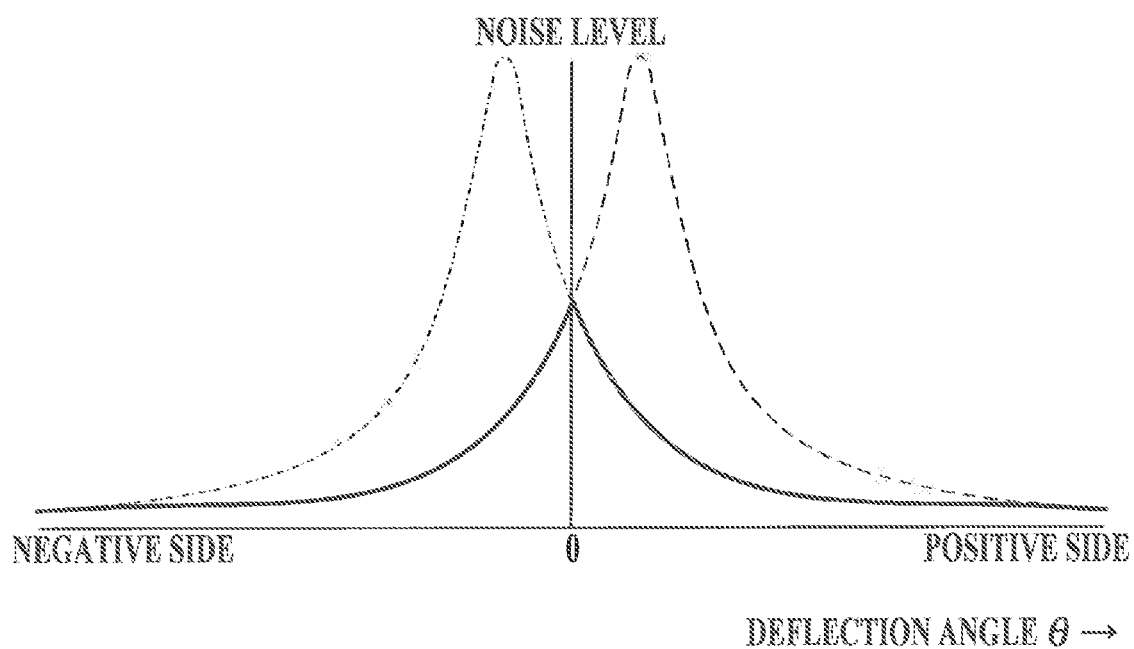

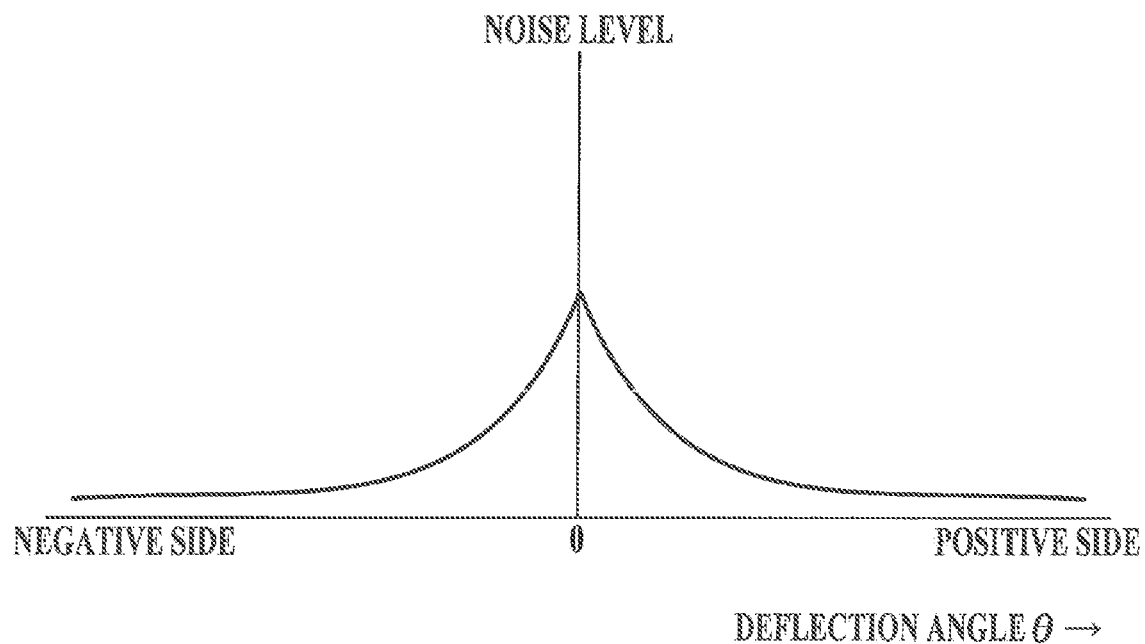

ULTRASOUND DIAGNOSTIC APPARATUS WITH ELECTROMAGNETIC NOISE SUPPRESSION

BACKGROUND OF THE INVENTION

Field of the Invention

The present invention relates to an ultrasound diagnostic apparatus.

Description of Related Art

With ultrasound diagnosis, it is possible to obtain with real time display the pulse of the heart or movement of a fetus by easy operation which is simply placing an ultrasound probe against a body surface. Moreover, since the examination is high in safety, the examination can be repeated many times.

As the image mode of the ultrasound diagnostic apparatus, there are a pulse Doppler mode and a continuous wave Doppler mode. The pulse Doppler mode is a mode which repeats one cycle of transmission of an ultrasound wave to a subject from an ultrasound probe and reception to obtain information such as flow rate of blood flow of a target in a subject. The continuous wave Doppler mode is a mode which divides and sets each transducer of the ultrasound probe between those for transmission and those for reception, and transmits and receives ultrasound from the ultrasound probe to the subject as necessary to obtain information such as flow rate of blood flow of a target in a subject.

Noise may be mixed in an electric reception signal generated in a reflecting ultrasound (echo) receiver of the ultrasound diagnostic apparatus. Such noise include electromagnetic noise such as, electromagnetic noise due to operation of an electric circuit inside the apparatus, electromagnetic noise due to an electromagnetic field outside the apparatus, and electric noise conducted from commercial power supply.

Therefore, there is known an ultrasound diagnostic apparatus in which a noise cancel range is set in a scanning direction in which noise of a B (Brightness) mode image is mixed and a reference signal corresponding to the noise detected in the noise cancel range cancels the noise included in the reception signal (see Japanese Patent No. 5459976).

There is also known an ultrasound diagnostic apparatus which switches the transducer for transmission so that the heated transducers are not fixed in the continuous wave Doppler mode (see Japanese Patent Application Laid-Open Publication No. 2006-223612).

The noise generated in the pulse Doppler mode in the conventional ultrasound image diagnostic apparatus is described with reference to FIG. 9A to FIG. 10. FIG. 9A shows noise generated when a deflection angle θ is positive in the conventional pulse Doppler mode. FIG. 9B shows noise generated when a deflection angle θ is 0° in the conventional pulse Doppler mode. FIG. 9C shows noise generated when a deflection angle θ is negative in the conventional pulse Doppler mode. FIG. 10 shows the noise level with respect to the deflection angle in the conventional pulse Doppler mode.

As shown in FIG. 9A, in the conventional ultrasound diagnostic apparatus, in the pulse Doppler mode, a Doppler gate (sample volume) is set with an operation inputter (not shown) in a position of a target T that the user desires to measure the blood flow rate in the subject. The deflection angle θ is calculated from the position of the Doppler gate. The deflection angle θ is an angle between a perpendicular line of an array direction passing through a central point of the array direction of a plurality of transducers 2a of the ultrasound probe 2 and the line connecting the central point of the array direction and the (central point of the) target of the subject. With the perpendicular line of the array direction as the standard, the deflection angle in the counter clockwise direction is to be positive and the angle in the clockwise direction is to be negative. When the deflection angle θ is positive, the ultrasound probe 2 uses the plurality of transducers 2a to output the transmission ultrasound U according to the electric transmission signal from a transmission deflector (not shown), receives an echo C from the target T, and converts the echo C to a plurality of electric echo signals E1. The plurality of echo signals E1 have a phase difference among each other according to a reception distance between each transducer 2a and the target T. Here, when noise N1 is mixed as the electromagnetic noise in the ultrasound probe 2, the phase of each noise N1 is uniform. A reception deflector 424 uses a plurality of reception delay interrupters 424a to provide delay time to the plurality of echo signals E1 and the plurality of noises N1 to make the phases of the plurality of echo signals E1 uniform. Therefore, the phases of the plurality of noises N1 do not become uniform. The length of the reception delay interrupter 424a in the horizontal direction shows delay time amount and the broken line represents off.

Then, the adder 424b adds a plurality of echo signals E1 and a plurality of noises N1, and outputs the echo signal E2 and noise N2. Since the phases of the plurality of echo signals E1 are uniform, the echo signal E2 becomes a signal larger than the echo signal E1, but since the phases of the plurality of noises N1 are not uniform, the noise N2 is suppressed more than the noise N1.

As shown in FIG. 9B, when the deflection angle θ is 0° in the pulse Doppler mode, since the reception distance between each transducer 2a and the target T are the same, the phases of the plurality of echo signals E1 are uniform. The reception deflector 424 uses the plurality of reception time interrupters 424a to provide the same amount of delay time to the plurality of echo signals E1 and the plurality of noises N1 to maintain the phases of the plurality of echo signals E1 uniform. However, since the phases of the noises N1 are uniform, the echo signal E2 and the noise N2 added and output by the adder 424b become a larger signal than the echo signal E1 and the noise N1.

As shown in FIG. 9C, when the deflection angle θ is negative in the pulse Doppler mode, the plurality of echo signals E1 have a phase difference among each other according to a reception distance between each transducer 2a and the target T. The reception deflector 424 uses the plurality of reception time interrupters 424a to provide delay time to the plurality of echo signals E1 and the plurality of noises N1 to make the phases of the plurality of echo signals E1 uniform. Therefore, the phases of the plurality of noises N1 do not become uniform. The echo signal E2 added and output by the adder 424b becomes a larger signal than the echo signal E1, and similarly, the noise N2 is suppressed more than the noise N1.

As shown in FIG. 10, the noise level of the noise N2 with respect to the deflection angle θ in the conventional pulse Doppler mode becomes the peak at θ=0°, and the noise level becomes higher as the absolute value of the deflection angle θ becomes smaller.

Next, the noise generated in the continuous wave Doppler mode in the conventional ultrasound diagnostic apparatus is described with reference to FIG. 11A to FIG. 12. FIG. 11A shows noise generated when a deflection angle θ is positive in the conventional continuous wave Doppler mode. FIG. 11B shows noise generated when a deflection angle θ is 0° in the conventional continuous wave Doppler mode. FIG. 11C shows noise generated when a deflection angle θ is negative in the conventional continuous wave Doppler mode. FIG. 12 shows the noise level with respect to the deflection angle in the conventional continuous wave Doppler mode.

As shown in FIG. 11A, according to the continuous wave Doppler mode in a conventional ultrasound diagnostic apparatus, a user sets with an operation inputter (not shown) a Doppler cursor (marker) in the direction of the target T that the user desires to measure the speed of the blood flow in the subject. The deflection angle θ is calculated from the direction of the Doppler cursor (marker). When the deflection angle θ is positive, the ultrasound probe 2 outputs a transmission ultrasound U with the transducer 2a fixed for transmission (3 transducers on the bottom half) according to the electric transmission signal from the transmission deflector (not shown). Then, the ultrasound probe 2 receives the echo C from the target T with the transducer 2a fixed for reception (3 transducers on the top half), and coverts the echo C to a plurality of electric echo signals E1. Here, the plurality of echo signals E1 have a phase difference among each other according to a reception distance between each transducer 2a and the target T. Here, when the noise N1 is mixed as the electromagnetic noise in the ultrasound probe 2, the phases of the noises N1 are uniform. The reception deflector 424 uses the plurality of reception delay interrupters 424a fixed for reception to provide delay time to the plurality of echo signals E1 and the plurality of noises N1 to make the phases of the plurality of echo signals E1 uniform. Therefore, the phases of the plurality of noises N1 are not uniform.

The adder 424b adds the plurality of echo signals E1, adds the plurality of noises N1, and outputs the echo signal E2 and noise N2. Since the phases of the plurality of echo signals E1 are uniform, the echo signal E2 is a larger signal than the echo signal E1. However, since the phases of the plurality of noises N1 are not uniform, the noise N2 is suppressed more than the noise N1.

As shown in FIG. 11B, when the deflection angle θ is 0° in the continuous wave Doppler mode, since the reception distance between each transducer 2a and the target T are different, there is a phase difference among the plurality of echo signals E1. The reception deflector 424 uses the plurality of reception delay interrupters 424a to provide delay time to the plurality of echo signals E1 and the plurality of noises N1 to make the phases of the plurality of echo signals E1 uniform. Therefore, the phases of the plurality of noises N1 are not uniform. The echo signal E2 added and output by the adder 424b becomes a signal larger than the echo signal E1 and the noise N2 is suppressed more than the noise N1.

As shown in FIG. 11C, when the deflection angle θ is negative in the continuous wave Doppler mode, since the reception distance between each transducer 2a and the target T is the same, the phases of the plurality of echo signal E1 are uniform. The reception deflector 424 uses the plurality of reception delay interrupters 424a to provide delay time to the plurality of echo signals E1 and the plurality of noises N1 to make the phases of the plurality of echo signals E1 uniform. However, since the phases of the noises N1 are not uniform, the echo signal E2 and the noise N2 added and output by the adder 424b become a signal larger than the echo signal E1 and the noise N1.

As shown in FIG. 12, the noise level of the noise N2 with respect to the deflection angle θ in the conventional continuous wave Doppler mode is shown with a solid line curve when the plurality of transducers 2a on the top half are fixed for reception, and with a broken line curve when the plurality of transducers 2a on the bottom half are fixed for reception. The solid line curve reaches a peak when the deflection angle θ is a predetermined negative value (the progressing direction of the echo C from the target T is the deflection angle parallel to the line perpendicular to the array direction), and as the absolute value of the difference between the deflection angle θ and the predetermined value becomes small, the noise level becomes high. The broken line curve reaches a peak when the deflection angle θ is a predetermined positive value (the progressing direction of the echo C from the target T is the deflection angle parallel to the line perpendicular to the array direction), and as the absolute value of the difference between the deflection angle θ and the predetermined value becomes small, the noise level becomes high.

The ultrasound diagnostic apparatus including the pulse Doppler mode and the continuous wave Doppler mode have high sensitivity to receive fine echo signals. However, as described above, since there is a deflection angle θ in which the noise level of the noise N2 becomes high, the apparatus has high sensitivity for the noise N2 in such deflection angle θ. Therefore, SN (Signal to Noise) ratio becomes low and there is a possibility that the accurate blood flow signal cannot be received.

According to the ultrasound diagnostic apparatus described in Japanese Patent Application Laid-Open Publication No. 2006-223612, it is not possible to improve the state of the SN ratio being low in the predetermined deflection angle θ in the pulse Doppler mode and the continuous wave Doppler mode. According to the ultrasound diagnostic apparatus described in Japanese Patent No. 549976, a circuit to detect noise is necessary. Components such as a shield, etc. become a reason for the apparatus to become larger, heavier, and more expensive, and the steps for manufacturing to increase. Therefore, there is a demand to suppress the number of physical components and to easily reduce image noise of the ultrasound image for the purpose of making the ultrasound diagnostic apparatus smaller, lighter, cheaper, and to reduce the steps for manufacturing.

BRIEF SUMMARY OF THE INVENTION

The present invention has been made in consideration of the above problems, and one of the main objects is to suppress the number of physical components while enhancing a SN ratio in an echo signal at a predetermined deflection angle θ.

In order to achieve at least one of the above-described objects, according to an aspect of the present invention, there is provided an ultrasound diagnostic apparatus which transmits and receives ultrasound from an ultrasound probe including a plurality of transducers to obtain information of a subject, the apparatus including:

a deflection controller which generates delay time information of delay amount to make phases of a plurality of reception signals input to each of a plurality of channels including the plurality of transducers uniform according to a deflection angle which is an angle between a perpendicular line of an array direction of the plurality of transducers, the line passing through a central point of the array direction and a line connecting the central point and a target of the subject;

a channel selector which selects according to the deflection angle a channel in which the reception signal of each channel is turned on or off so that the phases of the reception signals of each channel input to the plurality of channels are different and which generates channel selection information;

a reception delay interrupter which provides the delay amount to the reception signal of each channel according to the generated delay time information and which turns on or off the reception signal of each channel according to the generated channel selection information; and an adder which adds the plurality of reception signals which are provided with the delay amount and turned on.

Preferably, in the ultrasound diagnostic apparatus, transmission of a transmission signal transmitted to the ultrasound probe and reception of the reception signal configure one cycle, and the cycle is repeated.

Preferably, in the ultrasound diagnostic apparatus, the channel selector generates channel selection information to turn off the channel corresponding to the at least one transducer from one end of the array direction toward an inner side among the plurality of transducers.

Preferably, in the ultrasound diagnostic apparatus, the transmission of the transmission signal transmitted to the ultrasound probe and the reception of the reception signal are performed parallel simultaneously; and the channel selector turns off the channel corresponding to the transmission signal generating the channel selection information turning on the channel other than the channel turned off.

Preferably, the ultrasound diagnostic apparatus further includes, a storage which stores a table corresponding an image mode of ultrasound, a deflection angle, and an operation state of the reception delay interrupter corresponding to the delay time information and the channel selection information, wherein, the deflection controller obtains from the table an operation state according to the image mode and the deflection angle input by operation, and generates the delay time information based on the deflection angle and the obtained operation state; and the channel selector obtains from the table an operation state according to the image mode and the deflection angle input by operation, and generates the channel selection information based on the obtained operation state.

According to another aspect of the present invention, there is provided an ultrasound diagnostic apparatus which transmits and receives ultrasound from an ultrasound probe including a plurality of transducers to obtain information of a subject, the apparatus including:

a deflection controller which generates delay time information of delay amount to make phases of a plurality of reception signals input to each of a plurality of channels including the plurality of transducers uniform according to an acoustic line angle between a perpendicular line of an array direction of the plurality of transducers, the line passing through a central point of a reception opening of the plurality of transducers; and a line connecting a central point of the reception opening and a target of the subject;

a channel selector which selects according to the acoustic line angle a channel in which the reception signal of each channel is turned on or off so that the phases of the reception signals of each channel input to the plurality of channels are different and which generates channel selection information;

a reception delay interrupter which provides the delay amount to the reception signal of each channel according to the generated delay time information and which turns on or off the reception signal of each channel according to the generated channel selection information; and an adder which adds the plurality of reception signals which are provided with the delay amount and turned on.

According to another aspect of the present invention, there is provided an ultrasound diagnostic apparatus which transmits and receives ultrasound from an ultrasound probe including a plurality of transducers to obtain information of a subject, the apparatus including:

a deflection controller which generates delay time information of a plurality of reception signals input to a plurality of channels from the plurality of transducers; and a channel selector which controls on or off of the plurality of channels so that some of the plurality of transducers are selected as transmission transducers and transmit ultrasound from the transmission transducers, and some of the transducers other than the transmission transducers are selected as reception transducers and receive ultrasound with the reception transducers, wherein, when a position of a target of the subject is set to a side of the reception transducer, the channel selector switches the transmission transducer to the reception transducer and the reception transducer to the transmission transducer.

BRIEF DESCRIPTION OF THE DRAWINGS

The present invention will become more fully understood from the detailed description given hereinbelow and the appended drawings, and thus are not intended to define the limits of the present invention, and wherein;

FIG. 5 is a diagram showing a noise level with respect to a deflection angle in the pulse Doppler mode of the present embodiment;

FIG. 8 is a diagram showing a noise level with respect to the deflection angle in the continuous wave Doppler mode of the present embodiment;

DETAILED DESCRIPTION OF PREFERRED EMBODIMENTS

Figure 1:
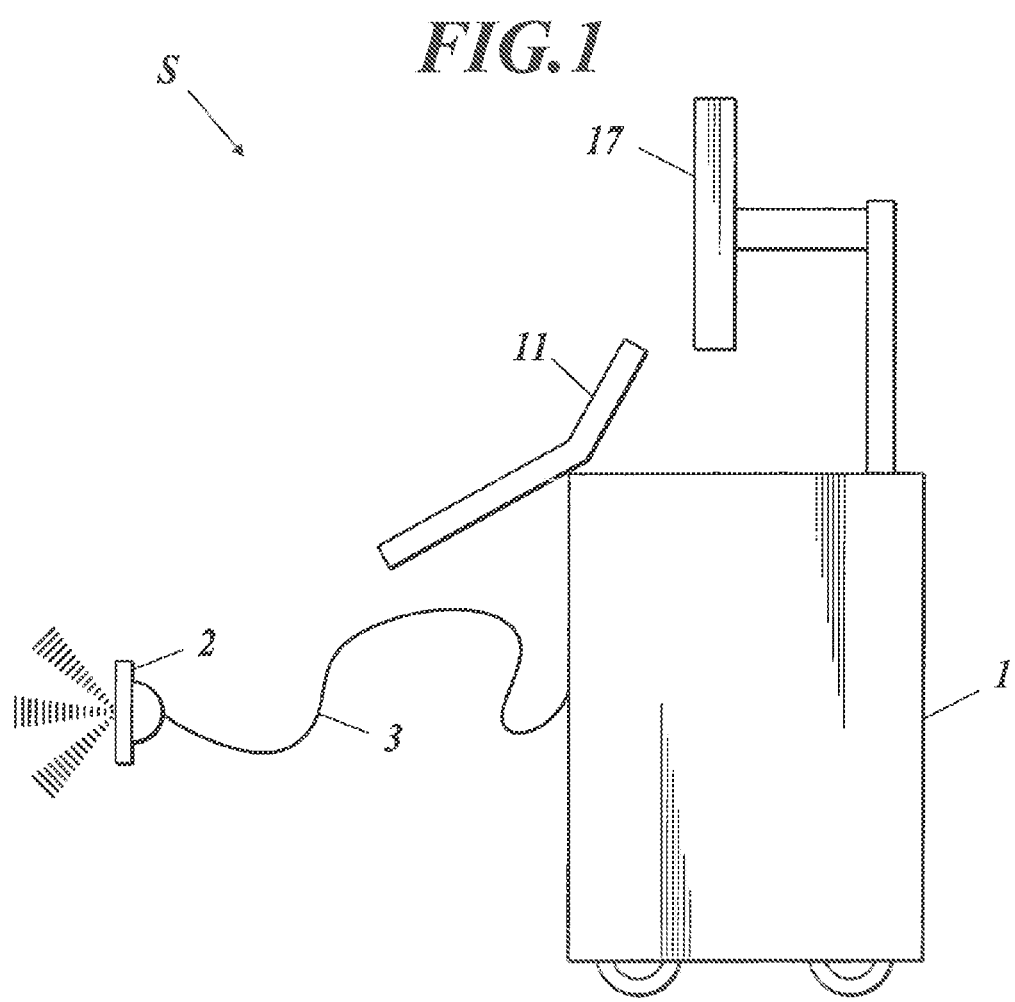
FIG. 1 is a diagram showing an exterior configuration of an ultrasound diagnostic apparatus.

The ultrasound image diagnostic apparatus of the embodiments of the present invention is described with reference to the drawings. However, the scope of the invention is not limited to the illustrated examples. In the description below, the same reference numerals are applied to the same functions and configurations, and the description is omitted.

Figure 2:
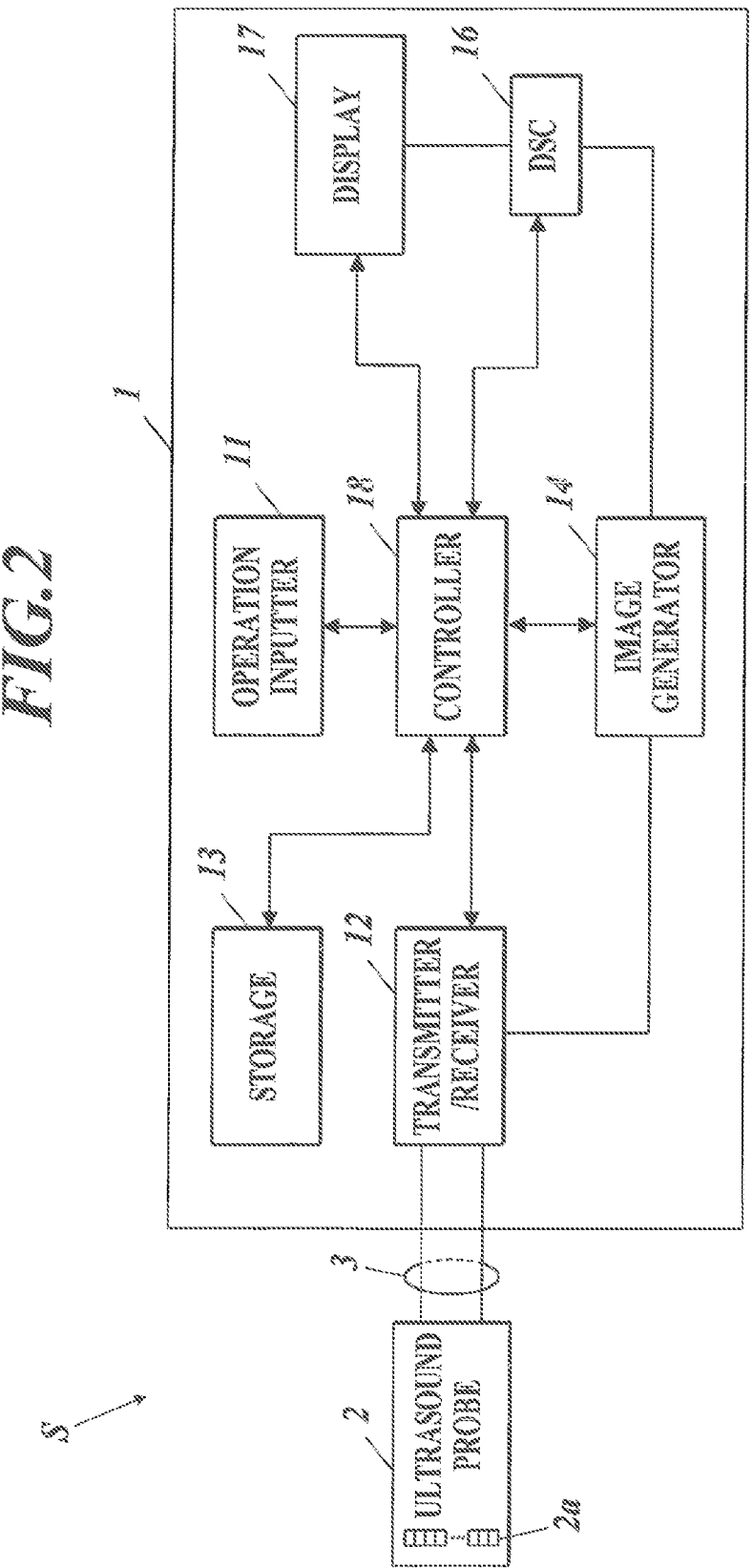
FIG. 2 is a block diagram showing an outline configuration of the ultrasound diagnostic apparatus.

FIG. 1 is a diagram showing an exterior configuration of an ultrasound image diagnostic apparatus S of the present embodiment. FIG. 2 is a block diagram showing an outline configuration of the ultrasound image diagnostic apparatus S. As shown in FIG. 1 and FIG. 2, the ultrasound image diagnostic apparatus S of the present embodiment includes an ultrasound image diagnostic apparatus main body 1 and an ultrasound probe 2. The ultrasound probe 2 transmits ultrasound (transmission ultrasound) to a subject such as a live body (not shown) and receives a reflected wave (reflected ultrasound: echo) of the ultrasound reflected on the subject. The ultrasound diagnostic apparatus main body 1 is connected to the ultrasound probe 2 through the cable 3. The ultrasound diagnostic apparatus main body 1 transmits an electric driving signal to the ultrasound probe 2 so that the ultrasound probe 2 transmits the echo to the subject and images as an ultrasound image an internal state of the subject based on a reception signal which is an electric signal generated in the ultrasound probe 2 according to the reflected ultrasound from the subject received in the ultrasound probe. The ultrasound image diagnostic apparatus main body 1 and the ultrasound probe 2 can also be connected by wireless communication means such as radio waves, infrared rays, etc.

The ultrasound image diagnostic apparatus S is able to set at least between a pulse Doppler mode and a continuous wave Doppler mode to obtain information of blood flow of a subject.

For example, the ultrasound probe 2 includes a backing layer, a piezoelectric layer, an acoustic matching layer, an acoustic lens, and the like in a layered state. The piezoelectric layer includes a transducer 2a as an electric acoustic converting element including a piezoelectric element. For example, a plurality of transducers 2a are arrayed in a one-dimensional array. According to the present embodiment, for example, an ultrasound probe 2 including 192 transducers 2a is used. The transducers 2a may be arrayed in a two-dimensional array. The number of transducers 2a can be set freely. According to the embodiment of the present invention, any type of ultrasound probe 2 can be used, such as a linear scanning type, a sector scanning type or a convex scanning type.

As shown in FIG. 2, for example, the ultrasound image diagnostic apparatus main body 1 includes an operation inputter 11, a transmitter/receiver 12, a storage 13, an image generator 14, a DSC (Digital Scan Converter) 16, a display 17, and a controller 18.

For example, the operation inputter 11 includes various switches, buttons, trackball, mouse, keyboard, etc. to input a command to instruct start of diagnosis, data such as personal information of the subject, and the like, and outputs an operation signal to the controller 18. The operation inputter 11 receives input such as mode setting information of the pulse Doppler mode and the continuous wave Doppler mode, setting of a Doppler gate in the pulse Doppler mode, and setting of a Doppler cursor (marker) in the continuous wave Doppler mode. A deflection angle θ is calculated in the controller 18 corresponding to the position and direction of the Doppler gate and the Doppler cursor (marker). The operator is able to directly input information of the deflection angle θ on the operation inputter 11.

The transmitter/receiver 12 is a circuit which supplies a transmission signal as the electric driving signal to the ultrasound probe 2 through the cable 3 to generate the transmission ultrasound in the ultrasound probe 2, receives an electric reception signal through the cable 3 from the ultrasound probe 2 which received the echo, and calculates the information such as flow rate of the blood flow according to the control of the controller 18. According to the control of the controller 18, in the pulse Doppler mode, the transmitter/receiver 12 sets the transducer 2a to which the transmission signal is supplied and delay time according to the deflection angle θ, supplies the transmission signal to the set transducer 2a provided with the set delay time, sets the transducer 2a from which the reception signal is obtained and the delay time according to the deflection angle θ, and receives the reception signal from the set transducer 2a and provides the delay time. The above set of transmission and reception is repeated.

According to control of the controller 18, in the continuous wave Doppler mode, the transmitter/receiver 12 sets the transducer 2a supplied with the transmission signal and the delay time according to the deflection angle θ, and supplies the transmission signal to the set transducer 2a provided with the set delay time. Together with the above transmission, the transmitter/receiver 12 sets the transducer 2a from which the reception signal is received and the delay time according to the deflection angle θ, and receives the reception signal from the set transducer 2a and provides the delay time. As described above, the transducer 2a to which the transmission signal is supplied and the transducer 2a from which the reception signal is obtained are different.

The storage 13 includes a flash memory, EEPROM (Electrically Erasable Programmable Read Only Memory) and stores various information.

The image generator 14 generates image data of a graph screen making the information such as flow rate of the blood flow of the reception signal from the transmitter/receiver 12 to a graph. The image data of the graph screen generated in the image generator 14 is output to the DSC 16.

The DSC 16 converts image data of the graph screen received from the image generator 14 to an image signal in a scanning format of a television signal and outputs the signal to the display 17.

The display 17 can be display apparatuses such as a LCD (Liquid Crystal Display), a CRT (Cathode-Ray Tube) display, an organic EL (Electronic Luminescence) display, an inorganic EL display, plasma display, and the like. The display 17 displays the image of the graph screen on the display screen according to the image signal output from the DSC 16.

For example, the controller 18 includes, a CPU (Central Processing Unit), a ROM (Read Only Memory), and a RAM (Random Access Memory). The controller 18 reads various processing programs such as a system program stored in the ROM, develops the program in the RAM and centrally controls the operation of each function of the ultrasound image diagnostic apparatus S according to the developed program. The ROM includes a nonvolatile memory such as a semiconductor, and stores a system program to handle the ultrasound image diagnostic apparatus S, various processing programs which can be executed on the system program, and various types of data. Such programs are stored in a form of a computer readable program code, and the CPU performs operation according to the program code. The RAM forms a work area which temporarily stores various programs performed by the CPU and data regarding such programs.

Figure 3:
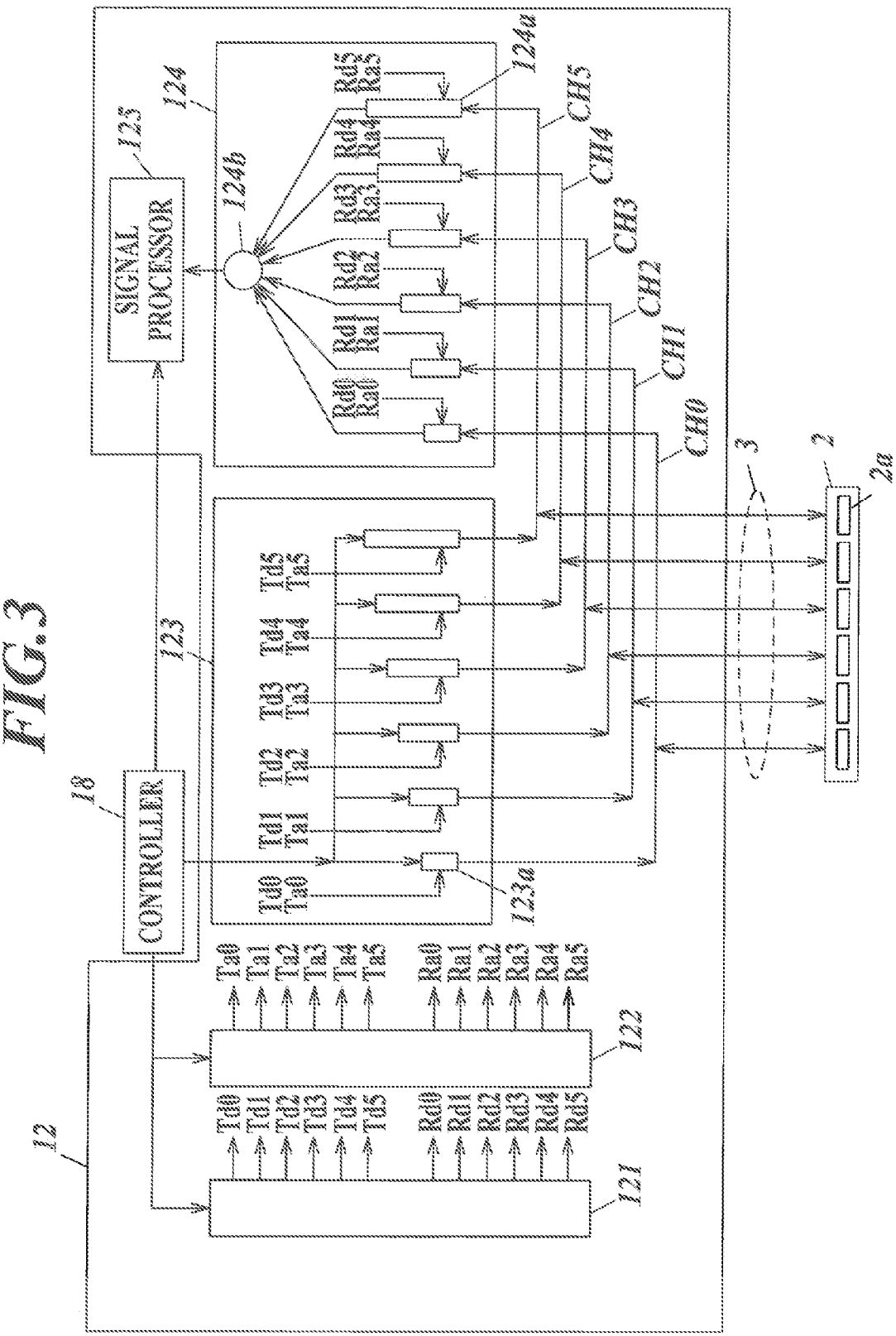
FIG. 3 is a block diagram showing a functional configuration of a transmitter/receiver.

Next, the configuration of the transmitter/receiver 12 is described with reference to FIG. 3. FIG. 3 is a block diagram showing a functional configuration of the transmitter/receiver 12.

As shown in FIG. 3, the transmitter/receiver 12 includes a deflection controller 121, a channel selector 122, a transmission deflector 123, a reception deflector 124, and a signal processor 125.

To simplify explanation, the ultrasound probe 2 connected to the transmitter/receiver 12 through the cable 3 includes 6 transducers 2a, and each corresponds to the following channels of the transmitter/receiver 12, channels CH0, CH1, CH2, CH3, CH4, and CH5. However, the number of transducers 2a and the number of channels of the transmitter/receiver 12 are not limited to the above.

The deflection controller 121 generates delay time information of each channel for transmission and reception according to the mode setting information and information of the deflection angle θ corresponding to the position of the Doppler gate and the direction of the Doppler cursor (marker) input from the controller 18. The deflection controller 121 outputs the delay time information for the transmission channels to a transmission delay interrupter 123a of each channel of the transmission deflector 123. The deflection controller 121 outputs the delay time information for the reception channels to a reception delay interrupter 124a of each channel of the reception deflector 124. The delay time information for each transmission channel is the delay time amount so that the transmission ultrasound output from the transducer 2a of each channel reaches the target at the same time. The delay time information of each reception channel is different depending on whether the state is the first to seventh state which depends on whether the mode is the pulse Doppler mode or the continuous wave Doppler mode and the deflection angle θ, and therefore this is described in detail later.

The channel selector 122 selects the transmission and reception channels to be turned on or off and generates channel selection information according to the mode setting information and the information regarding the deflection angle θ input from the controller 18. The channel selector 122 outputs channel selection information for the transmission channels to the transmission delay interrupter 123a of each channel of the transmission deflector 123. The channel selector 122 outputs channel selection information for the reception channels to the reception delay interrupter 124a of each channel of the reception deflector 124. The channel selection information of the transmission and reception channels in the pulse Doppler mode shows at least one of the channels is to be turned off. The channel selection information of the transmission channel in the continuous wave Doppler mode shows at least one channel is to be turned off, and the channel selection information of the reception channel in the continuous wave Doppler mode shows that the transmission channel turned off is to be turned on. Alternatively, in the continuous wave Doppler mode, at least one of the same channels for transmission and reception can be turned off.

The transmission deflector 123 generates the transmission signal from a transmission standard time signal input from the controller 18 and outputs the transmission signal to the transducer 2a of the ultrasound probe 2. The transmission deflector 123 includes a transmission delay interrupter 123a for each channel. The transmission delay interrupter 123a for each channel provides delay to the transmission standard time signal input from the controller 18 according to the delay time information Td0 to Td5 for each transmission channel input from the deflection controller 121, switches the on and off of the transmission standard time signal according to channel selection information Ta0 to Ta5 for each transmission channel input from the channel selector 122, and outputs the above as the transmission signal to the transducer 2a of each channel.

The reception deflector 124 provides delay and on or off to the reception signal input from the transducer 2a of the ultrasound probe 2 and adds the above. The reception deflector 124 includes a reception delay interrupter 124a for each channel and an adder 124b. The reception delay interrupter 124a for each channel provides delay to the reception signal input from the transducer 2a of each channel according to the delay time information Rd0 to Rd5 for each reception channel input from the deflection controller 121, switches the on and off of the reception signal according to the channel selection information Ra0 to Ra5 of each transmission channel input from the channel selector 122, and outputs the above to the adder 124b.

The adder 124b adds the reception signal input from the reception delay interrupter 124a of all channels. The signal process 125 uses the transmission reference time signal input from the controller 18 to calculate the information such as the flow rate of the blood flow by Fourier conversion from the added reception signal input from the adder 124b and outputs the result to the image generator 14.

Figure 4A:
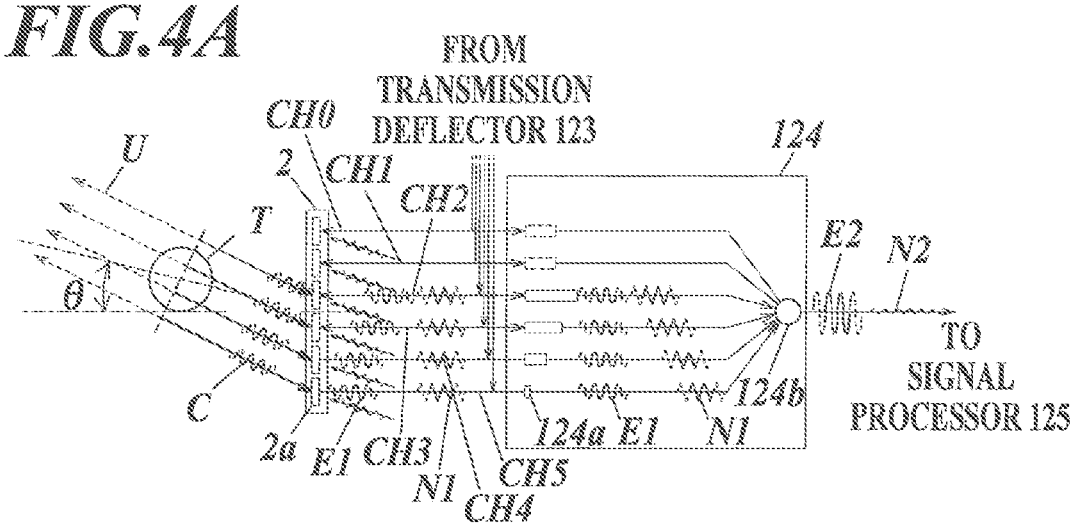
FIG. 4A is a diagram showing a first state of a transmitter/receiver when deflection angle $\theta<0°$ in a pulse Doppler mode of the present embodiment.
Figure 4B:
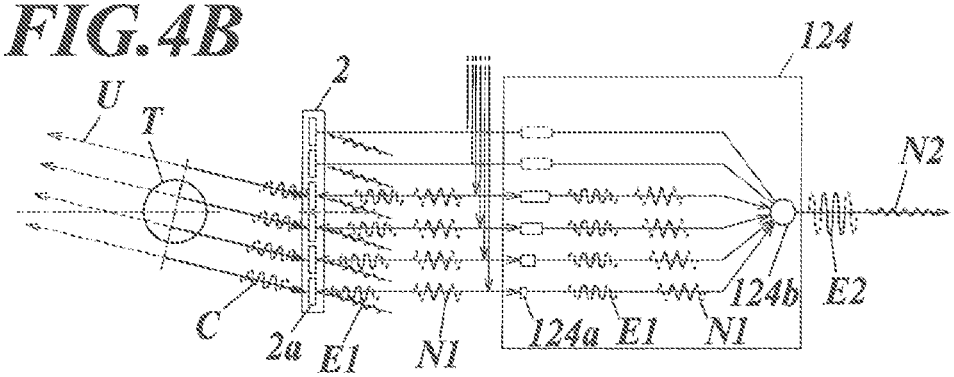
FIG. 4B is a diagram showing a second state of a transmitter/receiver when deflection angle $\theta \leq 0°$ in the pulse Doppler mode of the present embodiment.
Figure 4C:
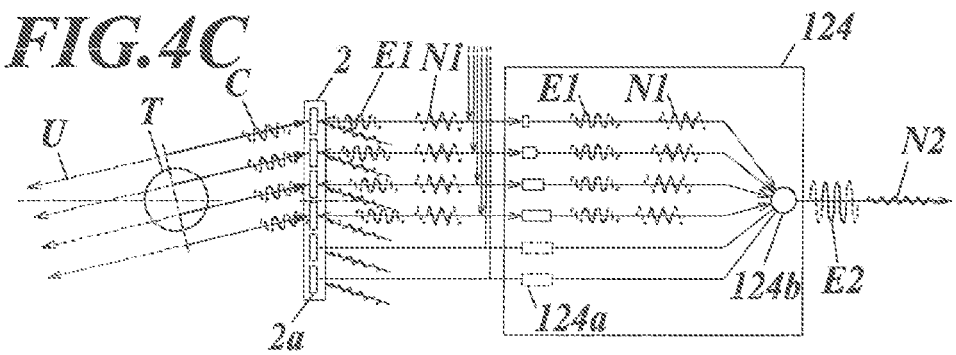
FIG. 4C is a diagram showing a third state of a transmitter/receiver when deflection angle $\theta \geq 0°$ in the pulse Doppler mode of the present embodiment.
Figure 4D:
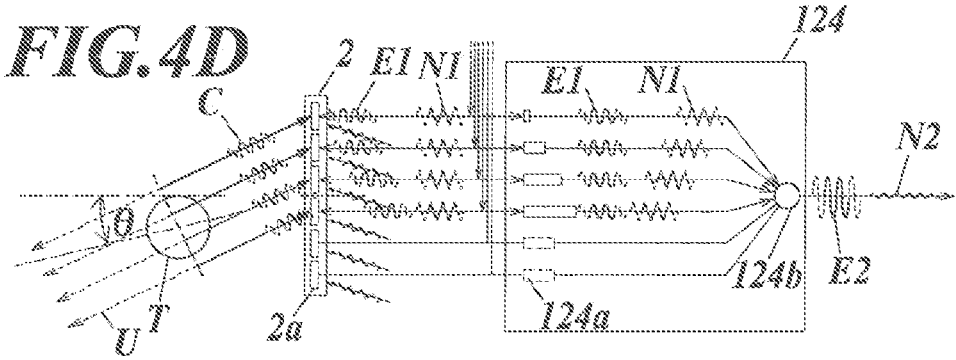
FIG. 4D is a diagram showing a fourth state of a transmitter/receiver when deflection angle $\theta>0°$ in the pulse Doppler mode of the present embodiment.

Next, the operation of the transmitter/receiver 12 of the ultrasound image diagnostic apparatus S in the pulse Doppler mode is described with reference to FIG. 4A to FIG. 5. FIG. 4A is a diagram showing a first state of the transmitter/receiver 12 when the deflection angle θ<0° in the pulse Doppler mode of the present embodiment. FIG. 4B is a diagram showing a second state of the transmitter/receiver 12 when the defection angle θ≤0° in the pulse Doppler mode of the present embodiment. FIG. 4C is a diagram showing a third state of the transmitter/receiver 12 when the deflection angle θ≥0° in the pulse Doppler mode of the present embodiment. FIG. 4D is a diagram showing a fourth state of the transmitter/receiver 12 when the deflection angle θ>0° in the pulse Doppler mode of the present embodiment. FIG. 5 is a diagram showing a noise level with respect to the deflection angle in the pulse Doppler mode of the present embodiment.

In the ultrasound image diagnostic apparatus S, in the pulse Doppler mode, the user inputs the mode setting information of the pulse Doppler mode and the deflection angle θ with the operation inputter 11. As shown in FIG. 4A, the operation state of the transmitter/receiver 12 when the deflection angle θ<0° (the deflection angle θ is negative and not near 0°) is to be the first state. In the first state and the later described second to fourth state, the transmission deflector 123 provides the delay time amount according to the delay time information from the deflection controller 121 and the on or off according to the channel selection information from the channel selector 122 to the transmission reference time signal input from the controller 18, and outputs the above as the transmission signal of each channel to the transducer 2a of each channel. In the first state, the transmission signal of the channels CH0 and CH1 is turned off by the transmission deflector 123.

The ultrasound probe 2 outputs transmission ultrasound U according to the transmission signal of each channel with the plurality of transducers 2a, receives the echo C from the target T, and converts the echo C to a plurality of echo signals E1 as the electric reception signal for each channel. There is a phase difference among the plurality of echo signals E1 according to the reception distance between each transducer 2a and the target T. Here, when noise N1 as the electromagnetic noise is mixed in the ultrasound probe 2, the phases of the noises N1 are uniform. The reception deflector 124 provides delay time amount according to the delay time information from the deflection controller 121 and the on or off according to the channel selection information from the channel selector 122 to the reception signal input from each transducer 2a, and makes the phases of the echo signals E1 uniform. Therefore, the phases of the plurality of noises N1 are not uniform. The delay time amount in the reception delay interrupter 124a of the channels CH2, CH3, CH4, and CH5 becomes smaller in order. The length of the reception delay interrupter 124a in the horizontal direction shows the delay time and the broken line represents off.

Then, the adder 124b adds the reception signal of each channel, and outputs the echo signal E2 and the noise N2 as the added transmission signal. The plurality of echo signals E1 and the plurality of noises N1 are added to output the echo signal E2 and the noise N2. Since the phases of the plurality of echo signals E1 are uniform, the echo signal E2 becomes a signal larger than the echo signal E1. Since the phases of the plurality of noises N1 are not uniform, the noise N2 is suppressed more than the noise N1.

Figure 9A:
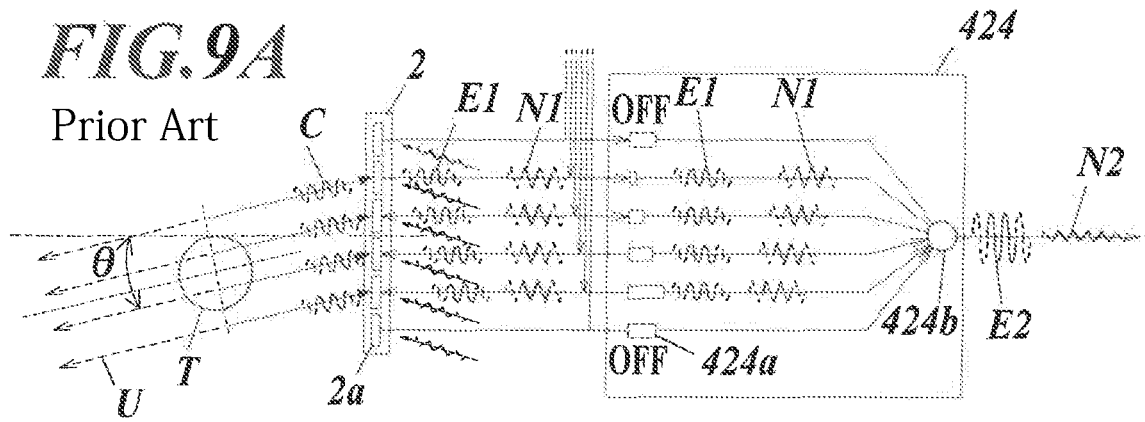
FIG. 9A is a diagram showing noise generation when the deflection angle θ is positive in the conventional pulse Doppler mode.
Figure 9B:
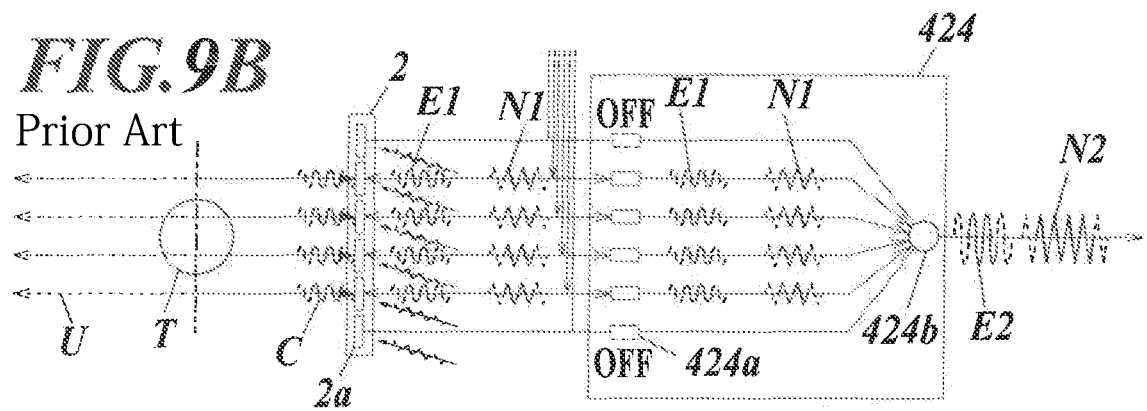
FIG. 9B is a diagram showing noise generation when the deflection angle θ is 0° in the conventional pulse Doppler mode.
Figure 9C:
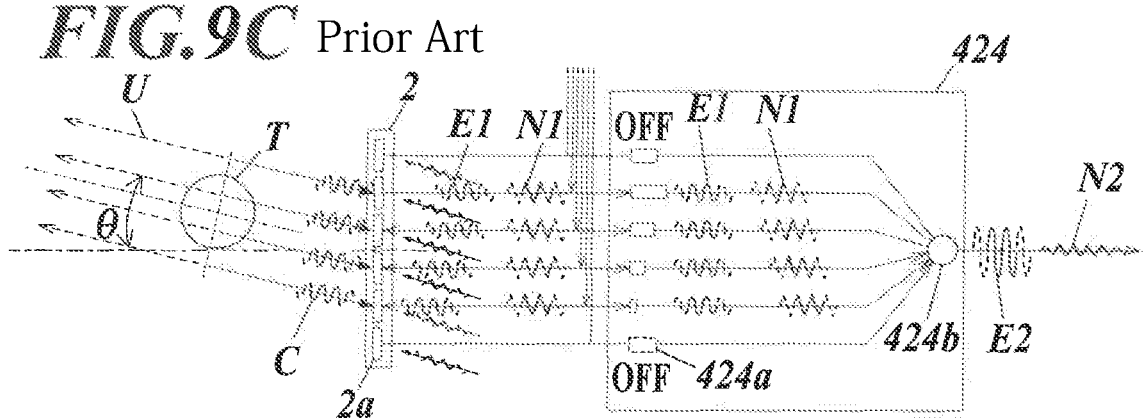
FIG. 9C is a diagram showing noise generation when the deflection angle θ is negative in the conventional pulse Doppler mode.
Figure 10:
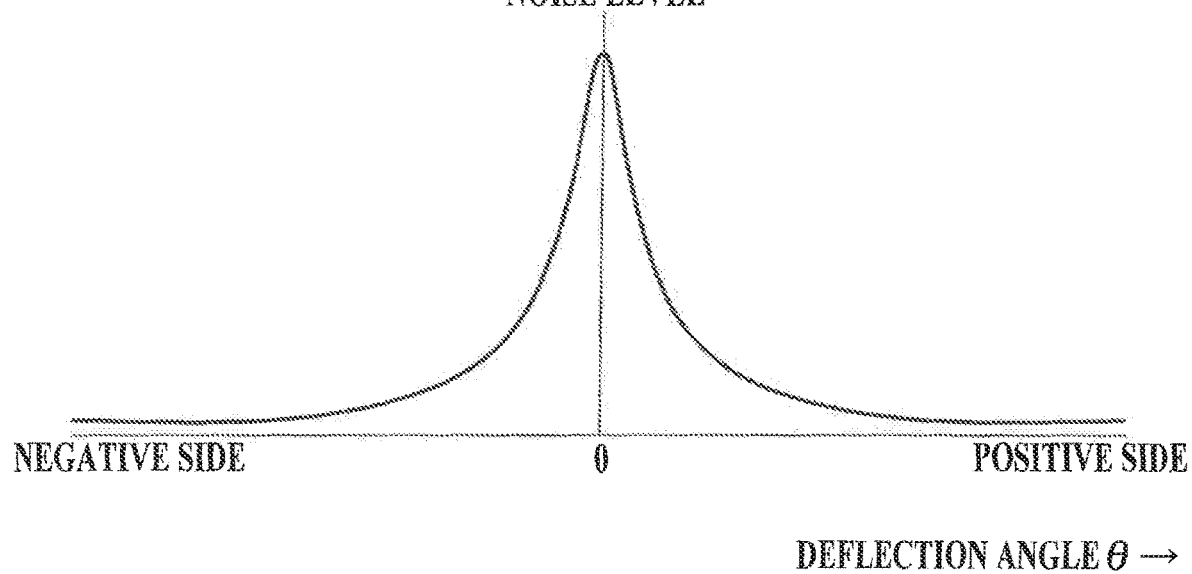
FIG. 10 is a diagram showing a noise level with respect to the deflection angle in the conventional pulse Doppler mode.

As shown in FIG. 4B, the operation state of the transmitter/receiver 12 when the deflection angle θ≤0° (the deflection angle θ is 0° or less and near 0°) is to be the second state. The second state is similar to the first state, but the delay time amount of the reception delay interrupter 124a of the channels CH2, CH3, CH4, and CH5 is smaller than the first state. In the second state also, the echo signal E2 becomes a larger signal, but the noise N2 is suppressed. Since the reception delay interrupter 124a of the channels CH0 and CH1 are turned off, the noise N2 does not become large when the deflection angle θ=0° as in FIG. 9B.

As shown in FIG. 4C, the operation state of the transmitter/receiver 12 when the deflection angle θ≥0° (the deflection angle θ is 0° or more and near 0°) is to be the third state. In the third state, the transmission deflector 123 provides a delay time amount according to the delay time information from the deflection controller 121 and the on or off according to the channel selection information from the channel selector 122 to the transmission reference time signal input from the controller 18, and outputs the above to the transducer 2a of each channel as the transmission signal of each channel. The transmission signals of the channels CH4 and CH5 are turned off.

The ultrasound probe 2 uses the plurality of transducers 2a to output the transmission ultrasound U according to the transmission signal of each channel, receives the echo C from the target T, and converts the echo C to the plurality of echo signals E1 as the electric reception signal of each channel. There is a phase difference among the plurality of echo signals E1 according to the reception distance between each transducer 2a and the target T. Here, when the noise N1 as the electromagnetic noise is mixed in the ultrasound probe 2, the phases of the noises N1 are uniform. The reception deflector 124 provides the delay time amount according to the delay time information from the deflection controller 121 and the on or off according to the channel selection information from the channel selector 122 to the reception signal input from each transducer 2a, and makes the phases of the echo signals E1 uniform. Therefore, the phases of the plurality of noises N1 are not uniform. The delay time amount in the reception delay interrupter 124a of the channels CH0, CH1, CH2, and CH3 become larger in order.

Then, the adder 124b adds the reception signal of each channel and outputs the echo signal E2 and the noise N2 as the added transmission signal. The plurality of echo signals E1 and the plurality of noises N1 are added to output the echo signal E2 and the noise N2. Since the phases of the plurality of echo signals E1 are uniform, the echo signal E2 is a signal larger than the echo signal E1. Since the phases of the plurality of noises N1 are not uniform, the noise N2 is suppressed more than the noise N1. Since the reception delay interrupter 124a of the channels CH4 and CH5 are turned off, the noise N2 does not become large when the deflection angle θ=0° as in FIG. 9B.

As shown in FIG. 4D, the operation state of the transmitter/receiver 12 when the deflection angle θ>0° (the deflection angle θ is 0° or more and not near 0°) is to be the fourth state. The fourth state is similar to the third state, but the delay time amount of the reception delay interrupter 124a of the channels CH0, CH1, CH2, and CH3 is larger than the third state. In the fourth state also, the echo signal E2 becomes a signal larger than the echo signal E1, but the noise N2 is suppressed more than the noise N1.

As shown in FIG. 5, the noise level of the noise N2 with respect to the deflection angle θ in the pulse Doppler mode of the present embodiment is reduced by switching the operation state. The alternate long and short dash line shown in FIG. 5 is a curve of a noise level when the deflection angle θ is changed in the fourth state. The peak of the curve in the long and short dash line is when the deflection angle θ is a negative predetermined value. The broken line shown in FIG. 5 is a curve of a noise level when the deflection angle θ is changed in the first state. The peak of the curve in the broken line is when the deflection angle θ is a positive predetermined value.

Therefore, the deflection controller 121 and the channel selector 122 control so that the first state is achieved when the deflection angle θ<0°, the second state is achieved when the deflection angle θ≤0°, the third state is achieved when the deflection angle θ≥0°, and the fourth state is achieved when the deflection angle θ>0°. The control is performed to achieve the second or third state when the deflection angle θ=0°. According to such control of the operation state, the noise level of the noise N2 is shown with the solid line curve in FIG. 5. Therefore, the noise level of the noise N2 is reduced with the control of the operation state shown with the solid line curve compared to the control of the operation state shown with the long and short dash line or the broken line.

The present embodiment is described from a different point of view.

In FIG. 4A and FIG. 4B, the channels CH2, CH3, CH4, and CH5 are selected in the transducer 2a and these channels are set as the opening of the ultrasound transmission and reception. The state of the noise changes depending on the angle (acoustic line angle) between a perpendicular line passing through a central point of the opening and a line connecting the central point of the opening and the target T.

As described in FIG. 5, the noise level reaches the peak when the perpendicular line passing through the central point of the opening and the target T are on the same line.

Therefore, if there is a certain angle between the perpendicular line passing through the central point of the opening and the target T, the phase of the noise of each channel is shifted, and therefore the noise is suppressed.

Turning to FIG. 4C and FIG. 4D, when the opening is set by the channels CH0, CH1, CH2, and CH3, the noise can be similarly suppressed if there is a certain angle between the perpendicular line of the central point of the opening and the angle of the target T.

Figure 6:
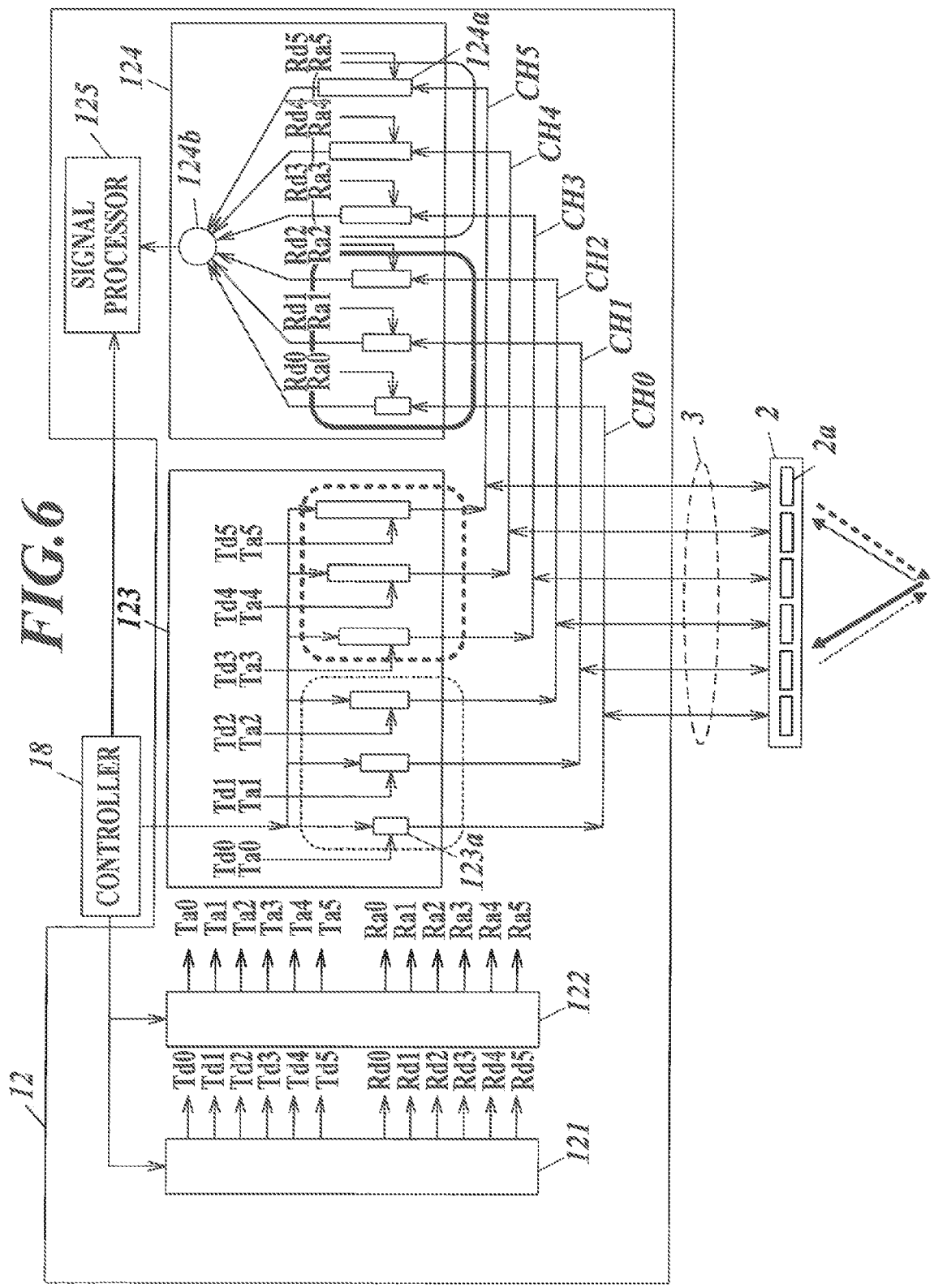
FIG. 6 is a diagram showing switching a channel in transmission and reception of a transmitter/receiver in a continuous wave Doppler mode of the present embodiment.
Figure 7A:
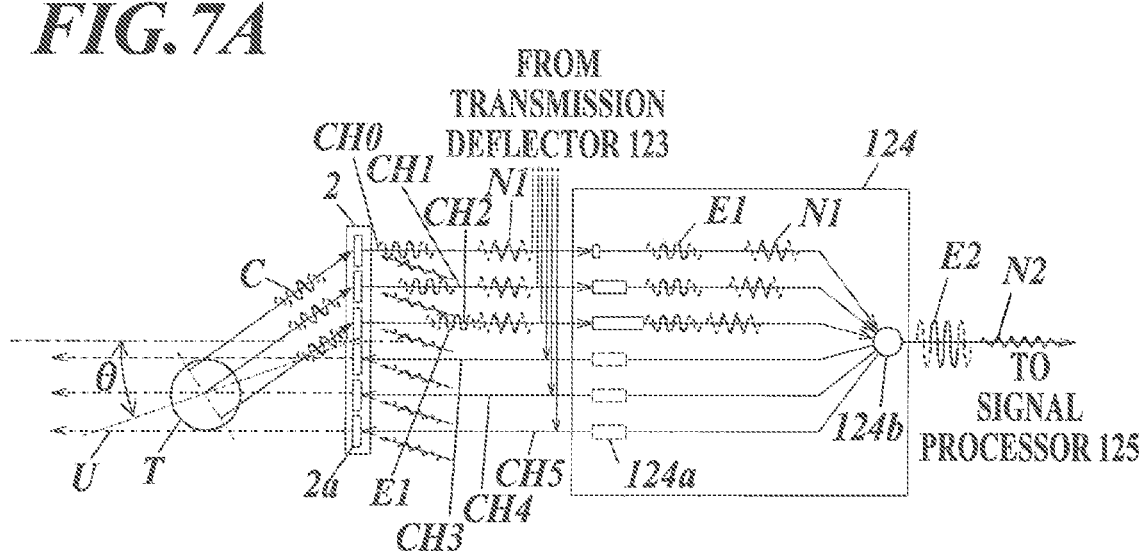
FIG. 7A is a diagram showing a fifth state of a transmitter/receiver when deflection angle $\theta>0°$ in the continuous wave Doppler mode of the present embodiment.
Figure 7B:
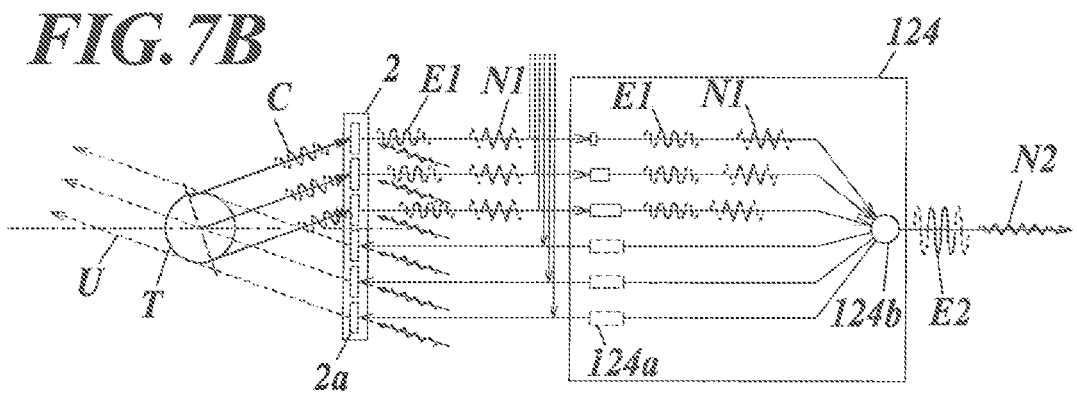
FIG. 7B is a diagram showing a sixth state of a transmitter/receiver when deflection angle $\theta=0°$ in the continuous wave Doppler mode of the present embodiment.
Figure 7C:
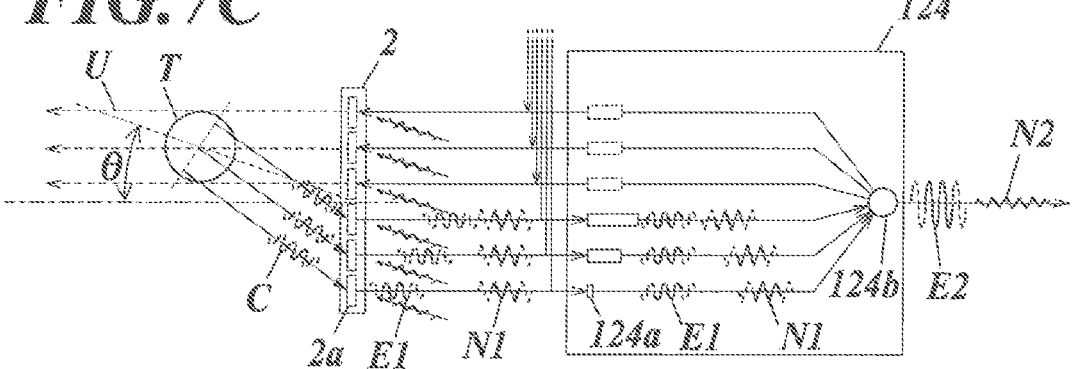
FIG. 7C is a diagram showing a seventh state of a transmitter/receiver when deflection angle $\theta<0°$ in the continuous wave Doppler mode of the present embodiment.

Next, the operation of the transmitter/receiver 12 in the ultrasound image diagnostic apparatus S in the continuous wave Doppler mode is described with reference to FIG. 6 to FIG. 8. FIG. 6 is a diagram showing switching of the channels in transmission and reception of the transmitter/receiver 12 in the continuous wave Doppler mode of the present embodiment. FIG. 7A is a diagram showing a fifth state of the transmitter/receiver 12 when the deflection angle θ>0° in the continuous wave Doppler mode of the present embodiment. FIG. 7B is a diagram showing a sixth state of the transmitter/receiver 12 when the deflection angle θ=0° in the continuous wave Doppler mode of the present embodiment. FIG. 7C is a diagram showing a seventh state of the transmitter/receiver 12 when the deflection angle θ<0° in the continuous wave Doppler mode of the present embodiment. FIG. 8 is a diagram showing noise level with respect to the deflection angle in the continuous wave Doppler mode of the present embodiment.

As shown in FIG. 6, in the continuous wave Doppler mode of the present embodiment, the channel of the reception deflector 124 (transmission deflector 123) is switched between 2 patterns according to the deflection angle θ. Specifically, when the deflection angle θ≥0°, the transmission channels of the transmission deflector 123 are set to the channels CH3, CH4, and CH5 (bold dotted line in FIG. 6), and the reception channels of the reception deflector 124 are set to the channels CH0, CH1, and CH2 which are the channels other than the channels CH3, CH4, and CH5 (bold solid line in FIG. 6). When the deflection angle θ<0°, the transmission channels of the transmission deflector 123 are set to the channels CH0, CH1, and CH2 (thin dotted line in FIG. 6), and the reception channels of the reception deflector 124 are set to the channels CH3, CH4, and CH5 which are the channels other than the channels CH0, CH1, and CH2 (thin solid line in FIG. 6).

In the continuous wave Doppler mode of the ultrasound image diagnostic apparatus S, the user inputs the mode setting information of the continuous wave Doppler mode, and the position and the direction of the Doppler cursor (marker) with the operation inputter 11, and based on the above, the controller 18 calculates the deflection angle θ. As shown in FIG. 7A, the operation state of the transmitter/receiver 12 when the deflection angle θ>0° is to be the fifth state. In the fifth state, the transmission deflector 123 provides the delay time amount according to the delay time information from the deflection controller 121 and the on or off according to the channel selection information from the channel selector 122 to the transmission reference time signal input from the controller 18, and outputs the above to the transducer 2a of each channel as the transmission signal of each channel. The transmission signals of the channels CH0, CH1, and CH2 are turned off.

The ultrasound probe 2 uses the plurality of transducers 2a to output the transmission ultrasound U according to the transmission signal of each channel, receives the echo C from the target T, and converts the echo C to the plurality of echo signals E1 as the electric reception signal of each channel. There is a phase difference among the plurality of echo signals E1 according to the distance between each transducer 2a and the target T. Here, when the noise N1 as the electromagnetic noise is mixed in the ultrasound probe 2, the phases of the noises N1 are uniform. The reception deflector 124 provides the delay time amount according to the delay time information from the deflection controller 121 and the on or off according to the channel selection information from the channel selector 122 to the reception signal input from the controller 18 and makes the phases of the echo signals E1 uniform. Therefore, the phases of the plurality of noises N1 are not uniform. The delay time amount in the reception delay interrupter 124a of the channels CH0, CH1, and CH2 becomes larger in order.

Then, the adder 124b adds the reception signal of each channel and outputs the echo signal E2 and the noise N2 as the added transmission signal. The plurality of echo signals E1 and the plurality of noises N1 are added to output the echo signal E2 and the noise N2. Since the phases of the plurality of echo signals E1 are uniform, the echo signal E2 becomes a signal larger than the echo signal 1. Since the phases of the plurality of noises N1 are not uniform, the noise N2 is suppressed more than the noise N1.

As shown in FIG. 7B, the operation state of the transmitter/receiver 12 when the deflection angle θ=0° is to be the sixth state. The sixth state is similar to the fifth state, but the delay time amount of the reception delay interrupter 124a of the channels CH0, CH1, and CH2 is smaller than the fifth state. In the sixth state also, the echo signal E2 becomes a signal larger than the echo signal E1, but the noise N2 is suppressed more than the noise N1.

As shown in FIG. 7C, the operation state of the transmitter/receiver 12 when the deflection angle θ<0° is to be the seventh state. In the seventh state, the transmission deflector 123 provides the delay time amount according to the delay time information from the deflection controller 121 and the on or off according to the channel selection information from the channel selector 122 to the transmission reference time signal input from the controller 18, and outputs the above to the transducer 2a of each channel as the transmission signal of each channel. The transmission signal of the channels CH3, CH4 and CH5 are turned off.

The ultrasound probe 2 uses the plurality of transducers 2a to output the transmission ultrasound U according to the transmission signal of each channel, receives the echo C from the target T, and converts the echo C to a plurality of echo signals E1 as the electric reception signal of each channel. There is a phase difference among the plurality of echo signals E1 according to the reception distance between each transducer 2a and the target T. Here, when the noise N1 as the electromagnetic noise is mixed in the ultrasound probe 2, the phases of the noises N1 are uniform. The reception deflector 124 provides the delay time amount according to the delay time information from the deflection controller 121 and the on or off according to the channel selection information from the channel selector 122 to the reception signal input from the controller 18 and makes the phases of the echo signals E1 uniform. Therefore, the phases of the plurality of noises N1 are not uniform. The delay time amount in the reception delay interrupter 124a of the channels CH3, CH4, and CH5 becomes smaller in order.

Figure 11A:
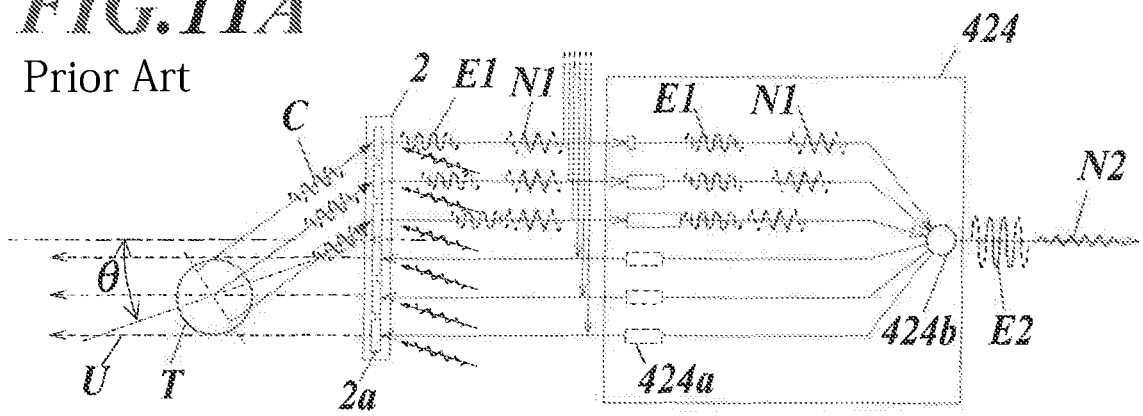
FIG. 11A is a diagram showing noise generation when the deflection angle θ is positive in the conventional continuous wave Doppler mode.
Figure 11B:
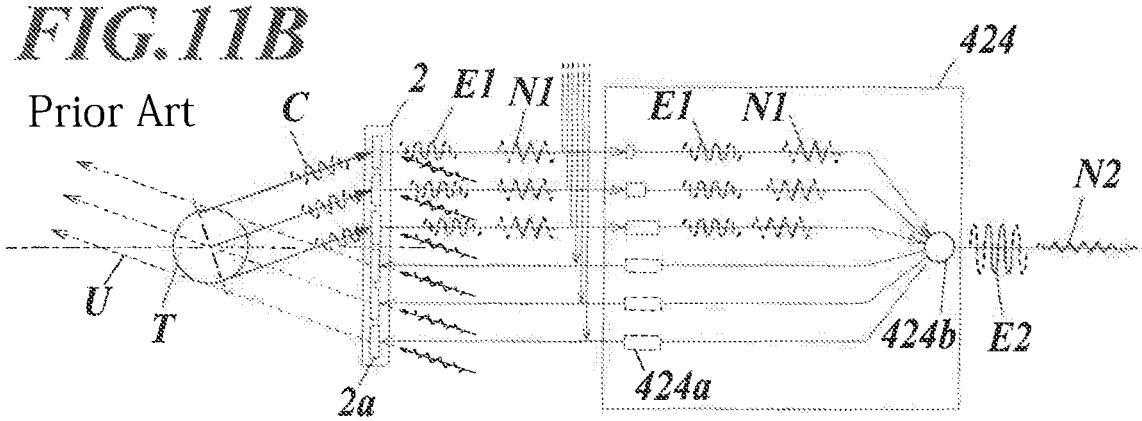
FIG. 11B is a diagram showing noise generation when the deflection angle θ is 0° in the conventional continuous wave Doppler mode.
Figure 11C:
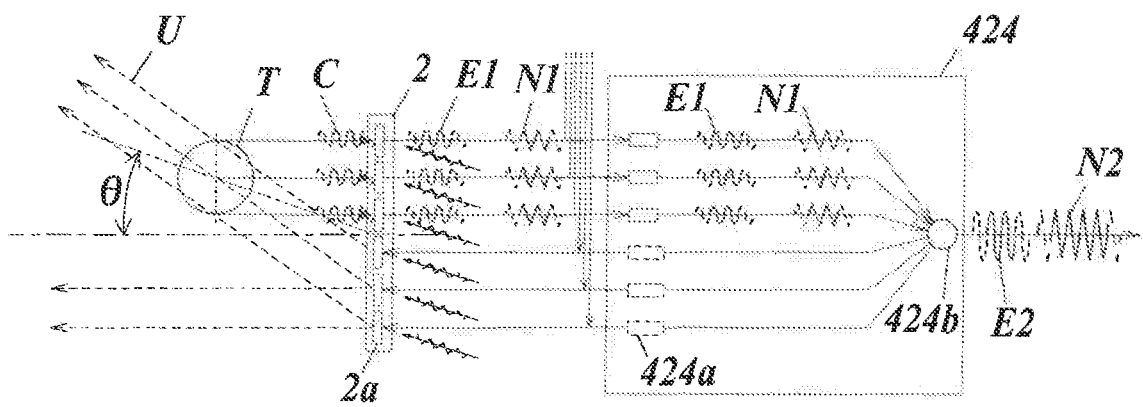
FIG. 11C is a diagram showing noise generation when the deflection angle θ is negative in the conventional continuous wave Doppler mode.

Then, the adder 124b adds the reception signal of each channel and outputs the echo signal E2 and the noise N2 as the added transmission signal. The plurality of echo signals E1 and the plurality of noises N1 are added to output the echo signal E2 and the noise N2. Since the phases of the plurality of echo signals E1 are uniform, the echo signal E2 becomes a signal larger than the echo signal E1. Since the phases of the plurality of noises N1 are uniform, the noise N2 is suppressed more than the noise N1. Since the reception delay interrupter 124a of the channels CH0, CH1, and CH2 is turned off, the noise N2 does not become large when the deflection angle θ<0° as in FIG. 11C.

As shown in FIG. 8, the noise level of the noise N2 with respect to the deflection angle θ in the continuous wave Doppler mode of the present embodiment is reduced by switching the operation state.

Figure 12:
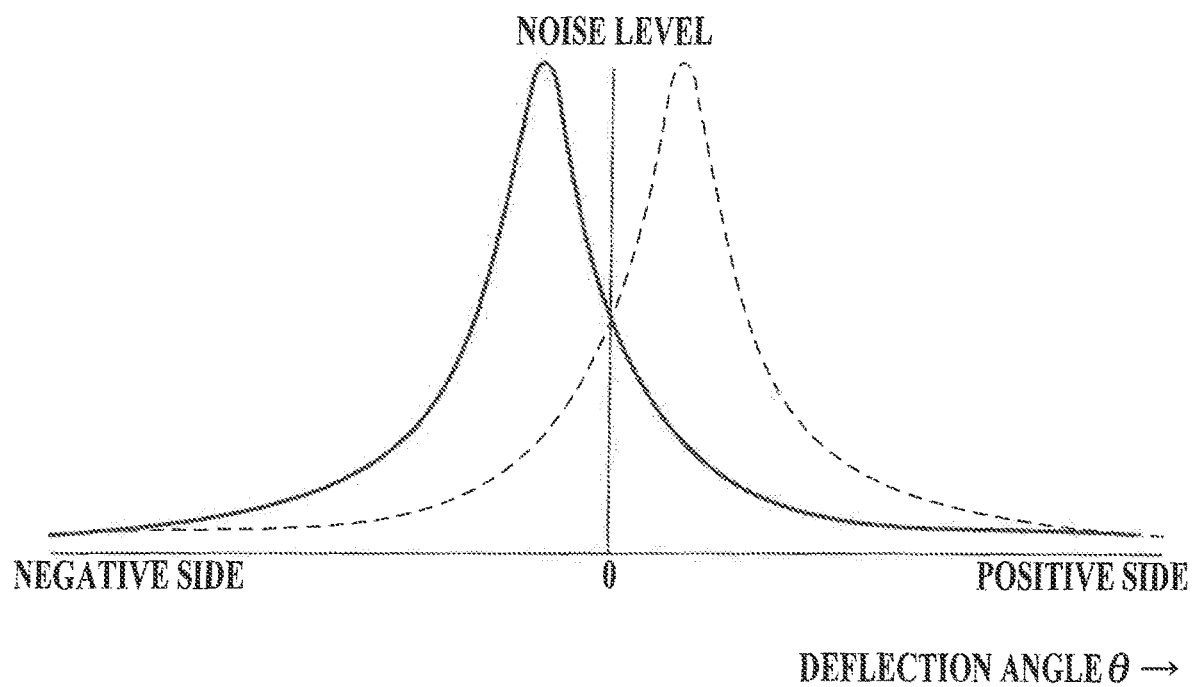
FIG. 12 is a diagram showing noise level with respect to the deflection angle in the conventional continuous wave Doppler mode.

The deflection controller 121 and the channel selector 122 control so that the fifth state is achieved when the deflection angle θ>0°, the sixth state is achieved when the defection angle θ=0°, and the seventh state is achieved when the deflection angle θ<0°. According to such control of the operation state, the noise level of the noise N2 is shown with the solid line curve in FIG. 8. The solid line curve in FIG. 8 is the curve with the smaller value between the solid line curve and the dotted line curve in FIG. 12.

According to the present embodiment, the ultrasound image diagnostic apparatus S uses the deflection controller 121 to generate delay time information of the delay amount according to the deflection angle θ to make the phases of the plurality of reception signals input in each of the plurality of channels composing the plurality of transducers 2a uniform and to output the above to the reception delay interrupter 124a. The ultrasound image diagnostic apparatus S uses the channel selector 122 to select the channel in which the reception signal of each channel is turned on or off according to the deflection angle θ so that the phase of the reception signal in each channel input in the plurality of channels become different, to generate the channel selection information, and to output the above to the reception delay interrupter 124a. Then, the ultrasound image diagnostic apparatus S uses the reception delay interrupter 124a to provide delay amount to the reception signal of each channel received in the plurality of channels from the plurality of transducers 2a according to the input delay time information, and to perform on or off of the reception signal of each channel according to the input channel selection information. The adder 124b is used to add the reception signal provided with the delay amount and turned on.

Therefore, physical components such as a shield for noise cancelling can be suppressed, and the ultrasound image diagnostic apparatus S can be made smaller, lighter, cheaper, and the steps for manufacturing can be reduced. Moreover, the noise in the predetermined deflection angle θ can be suppressed and the SN ratio of the echo signal can be enhanced.

In the pulse Doppler mode, the transmission of the transmission signal transmitted to the ultrasound probe and the reception of the reception signal compose 1 cycle and the cycle is repeated. Therefore, in the pulse Doppler mode, the physical component can be suppressed, and the noise in the deflection angle θ=0° can be suppressed and the SN ratio of the echo signal can be enhanced.

The channel selector 122 generates the channel selection information to turn off the channels CH0 and CH1 corresponding to the 2 transducers 2a at one end of the array direction of the plurality of transducers 2a. Therefore, in the pulse Doppler mode, it is possible to prevent the operation state in which the noise N2 become large as shown in the conventional FIG. 9B, and it is possible to suppress the noise when the deflection angle θ=0°, and to enhance the SN ratio of the echo signal. Alternatively, the channel corresponding to 1 or 3 or more transducers 2a at one end of the array direction of the plurality of transducers 2a may be turned off.

In the continuous wave Doppler mode, the transmission of the transmission signal and the reception of the reception signal are performed at the same time, the channel selector 122 turns off the channel corresponding to the transmission signal, and generates channel selection information which turns on the channel other than the channel turned off. Therefore, in the continuous wave Doppler mode, the noise in the deflection angle θ<0° can be suppressed, and the SN ratio of the echo signal can be enhanced.

As one of the embodiments of the continuous wave Doppler mode, some of the plurality of transducers 2a can be used for transmission and the others can be used for reception. For example, the plurality of transducers 2a from one end to the center are used for transmission and those remaining are used for reception.

Here, when the position and the direction of the target T of the subject are set with a Doppler marker, and the position of the target T is detected to be in the side of the reception transducers, the transmission transducers here are used for reception, the reception transducers here are used for transmission, and the transmission and reception are switched. With this, the deflection angle θ can be set to an angle suitable for suppressing noise, and the effect of suppressing noise can be enhanced.

The description of the above-described embodiments is one example of the suitable ultrasound diagnostic apparatus according to the present invention, and the present invention is not limited to the above.

For example, according to the present embodiment, in the ultrasound image diagnostic apparatus S, the deflection controller 121 and the channel selector 122 generate the delay time information and the channel selection information according to information from the controller 18 regarding the pulse Doppler mode or the continuous wave Doppler mode and the deflection angle θ input from the user on the operation inputter 11. However, the present invention is not limited to the above. For example, the storage 13 can store a table corresponding the ultrasound image mode (pulse Doppler mode or continuous wave Doppler mode), the deflection angle θ, and the operation state (first state to seventh state) corresponding to the delay time information and the channel selection information.

According to such configuration, when the user inputs the information regarding the pulse Doppler mode or the continuous wave Doppler mode, and the Doppler gate or the Doppler cursor on the operation inputter 11, the controller 18 calculates the deflection angle θ, reads out the table from the storage 13, obtains the operation state of the transmitter/receiver 12 (reception delay interrupter 124a) corresponding to the input ultrasound image mode and the deflection angle θ from the table, and outputs the above to the deflection controller 121 and the channel selector 122. The deflection controller 121 generates the delay time information according to the deflection angle θ and the operation state input from the controller 18. The channel selector 122 generates the channel selection information according to the operation state input from the controller 18. According to such configuration, the delay time information and the channel selection information can be easily generated. The deflection angle θ when the operation state is switched and the operation state switched to may be different according to the ultrasound image diagnostic apparatus (according to machine type). In this case, by rewriting the information of the table in the storage 13, the control of the operation state can be easily and suitably adjusted according to the ultrasound diagnostic apparatus.

According to the above-described embodiments, in the pulse Doppler mode, the channel which transmits transmission signals and the channel which receives reception signals are completely the same. However, the present invention is not limited to the above. In the pulse Doppler mode, at least one of the channels which transmits the transmission signals and at least one of the channels which receive the reception signal are to be the same.

The detailed configuration and operation of each unit composing the ultrasound image diagnostic apparatus S according to the present embodiment can be suitably modified without leaving the scope of the present invention.

The present U.S. patent application claims priority under the Paris Convention of Japanese Patent Application No. 2015-002790 filed on Jan. 9, 2015 the entirety of which is incorporated herein by reference.

What is claimed is:

1. An ultrasound diagnostic apparatus which transmits and receives ultrasound from an ultrasound probe including a plurality of transducers to obtain information of a subject, the apparatus comprising:
   a plurality of channels corresponding to the plurality of transducers and respectively connectable to the plurality of transducers;
   a deflection controller configured to generate delay time information of delay amounts for transmission and reception on the plurality of channels according to a deflection angle, wherein the deflection angle being an angle between a perpendicular line of an array direction of the plurality of transducers, the perpendicular line passing through a central point of the array direction, and a line connecting the central point and a target of the subject;
   a channel selector configured to select, according to the deflection angle, reception channels of the plurality of channels that are to be turned on for reception of reception signals on the reception channels, the channel selector being configured to generate channel selection information;
   a reception delay interrupter configured to provide the delay amount to the reception signal of each of the reception channels according to the generated delay time information and configured to turn on the reception signal of each of the reception channels for reception of the reception signals according to the generated channel selection information, the delay amounts for the reception channels are based on reception distances between each of the transducers of the reception channels and the target, and the delay amounts make phases of the reception signals input into the reception channels uniform and phases of electromagnetic noise signals input into the reception channels non-uniform; and
   an adder which is configured to add the plurality of reception signals which are provided with the delay amounts on the reception channels and the plurality of noise signals which are provided with the delay amounts on the reception channels, wherein the reception channels of the plurality of channels define an opening of ultrasound reception and the reception channels are selected by the channel selector so that an acoustic line angle between a perpendicular line passing through a central point of the opening and a line connecting the central point of the opening and the target is equal or greater than a predetermined angle that is not zero and that ensures that phases of electromagnetic noise on the reception channels are shifted by the delay amounts and the electromagnetic noise is suppressed.

2. The ultrasound diagnostic apparatus of claim 1, wherein, transmission of a transmission signal transmitted to the ultrasound probe and reception of a reception signal is one cycle, and the cycle is repeated.

3. The ultrasound diagnostic apparatus of claim 2, wherein,
   transmission of the transmission signal transmitted to the ultrasound probe and reception of the reception signal are performed in parallel and simultaneously in a Doppler mode; and
   the reception channels selected by the channel selector are other than channels of the plurality of channels set for the transmission signal.

4. The ultrasound diagnostic apparatus of claim 1, wherein, the channel selector is configured to generate channel selection information to turn off the channel corresponding to at least one transducer from one end of the array direction toward an inner side among the plurality of transducers.

5. The ultrasound diagnostic apparatus of claim 1, further comprising,
   a storage configured to store a table corresponding an image mode of ultrasound, a deflection angle, and an operation state of the reception delay interrupter corresponding to the delay time information and the channel selection information,
   wherein,
   the deflection controller is configured to obtain from the table the operation state according to the image mode and the deflection angle input by operation, and generates the delay time information based on the deflection angle and the obtained operation state; and
   the channel selector is configured to obtain from the table an operation state according to the image mode and the deflection angle input by operation, and generates the channel selection information based on the obtained operation state.

6. The ultrasound diagnostic apparatus of claim 1, wherein
   the reception channels selected by the channel selector are the same as channels of the plurality of channels set for the transmission signal in a pulse Doppler mode and the reception channels selected by the channel selector are other than the channels of the plurality of channels set for the transmission signal in a continuous wave Doppler mode.

7. An ultrasound diagnostic apparatus which transmits and receives ultrasound from an ultrasound probe including a plurality of transducers to obtain information of a subject, the apparatus comprising:
- a plurality of channels corresponding to the plurality of transducers and respectively connectable to the plurality of transducers;
- a deflection controller configured to generate delay time information of delay amounts for transmission and reception on the plurality of channels according to a acoustic line angle to, wherein the acoustic line angle being an angle between a perpendicular line of an array direction of the plurality of transducers, the perpendicular line passing through a central point of the array direction, and a line connecting the central point and a target of the subject;
- a channel selector configured to select, according to the acoustic line angle, reception channels of the plurality of channels that are to be turned on for reception of reception signals on the reception channels, the channel selector being configured to generate channel selection information;
- a reception delay interrupter configured to provide the delay amount to the reception signal of each of the reception channels according to the generated delay time information and configured to turn on the reception signal of each of the reception channels for reception of the reception signals according to the generated channel selection information, the delay amounts for the reception channels are based on reception distances between each of the transducers of the reception channels and the target, and the delay amounts make phases of the reception signals input into the reception channels uniform and phases of electromagnetic noise signals input into the reception channels non-uniform; and
- an adder which is configured to add the plurality of reception signals which are provided with the delay amounts on the reception channels and turned on and the plurality of noise signals which are provided with the delay amounts on the reception channels, wherein the reception channels of the plurality of channels define an opening of ultrasound reception and the reception channels are selected by the channel selector so that an acoustic line angle between a perpendicular line passing through a central point of the opening and a line connecting the central point of the opening and the target is equal or greater than a predetermined angle that is not zero and that ensures that phases of electromagnetic noise on the reception channels are shifted by the delay amounts and the electromagnetic noise is suppressed.

8. An ultrasound diagnostic apparatus which transmits and receives ultrasound from an ultrasound probe including a plurality of transducers to obtain information of a subject, the apparatus comprising:
- a plurality of channels corresponding to the plurality of transducers and respectively connectable to the plurality of transducers;
- a deflection controller configured to generate delay time information of a plurality of reception signals input to the plurality of channels from the plurality of transducers; and
- a channel selector configured to control on or off each of the plurality of channels so that some of the plurality of transducers are selected as transmission transducers and transmit ultrasound from the transmission transducers, and some of the transducers other than the transmission transducers are selected as reception transducers and receive ultrasound with the reception transducers,
wherein, when a position of a target of the subject is set to a side of one of the reception transducers, the channel selector switches one of the transmission transducers to the reception transducer and one of the reception transducers to the transmission transducer, and
wherein the reception transducers of the plurality of channels define an opening of ultrasound reception, the delay amounts for the reception channels are based on reception distances between each of the transducers of the reception channels and the target, and the delay amounts make phases of the reception signals input into the reception channels uniform and phases of electromagnetic noise signals input into the reception channels non-uniform, and the reception transducers are selected by the channel selector so that an acoustic line angle between a perpendicular line passing through a central point of the opening and a line connecting the central point of the opening and the target is equal or greater than a predetermined angle that is not zero and that ensures that phases of electromagnetic noise on reception channels of the plurality of channels connected to the reception transducers are shifted by the delay time information generated by the deflection controller and the electromagnetic noise is suppressed.

* * * * *